United States Patent
Dinse et al.

(10) Patent No.: US 10,182,779 B2
(45) Date of Patent: Jan. 22, 2019

(54) MEDICAL SYSTEM

(71) Applicant: SIEMENS HEALTHCARE GMBH, Erlangen (DE)

(72) Inventors: Franziska Dinse, Heiligenstadt (DE); Michael Fuhrmann, Herzogenaurach (DE); Alexander Langenbucher, Bayreuth (DE); Juliane Ritter, Neunkirchen (DE); Hans Schweizer, Plattling (DE)

(73) Assignee: Siemens Healthcare GmbH, Erlangen (DE)

( * ) Notice: Subject to any disclaimer, the term of this patent is extended or adjusted under 35 U.S.C. 154(b) by 68 days.

(21) Appl. No.: 15/024,455

(22) PCT Filed: Jul. 3, 2014

(86) PCT No.: PCT/EP2014/064146
§ 371 (c)(1),
(2) Date: Mar. 24, 2016

(87) PCT Pub. No.: WO2015/043783
PCT Pub. Date: Apr. 2, 2015

(65) Prior Publication Data
US 2016/0242716 A1 Aug. 25, 2016

(30) Foreign Application Priority Data
Sep. 24, 2013 (DE) .......... 10 2013 219 194

(51) Int. Cl.
*A61B 6/00* (2006.01)
*G16H 40/63* (2018.01)
*G06F 19/00* (2018.01)

(52) U.S. Cl.
CPC .......... *A61B 6/467* (2013.01); *A61B 6/462* (2013.01); *G06F 19/00* (2013.01); *G16H 40/63* (2018.01)

(58) Field of Classification Search
None
See application file for complete search history.

(56) References Cited

U.S. PATENT DOCUMENTS

| 5,394,871 A | 3/1995 | Sauer et al. |
| 7,113,836 B2 | 9/2006 | Hoernig |
| 2005/0251228 A1 | 11/2005 | Hamel |

(Continued)

FOREIGN PATENT DOCUMENTS

| CN | 102836007 A1 | 12/2012 |
| DE | 4220923 A1 | 1/1994 |

(Continued)

*Primary Examiner* — Hoon Song
(74) *Attorney, Agent, or Firm* — Laurence Greenberg; Werner Stemer; Ralph Locher

(57) ABSTRACT

A medical system includes a plurality of movable elements, a first control element for controlling a first type of movement and at least one further control element for controlling a further type of movement. The first control element is assigned to a first number of movable elements for controlling the first type of movement and the further control elements are assigned to a further number of movable elements for controlling the further type of movement. The control elements each include an input unit having at least two selection elements for selecting the movable element to be controlled.

9 Claims, 1 Drawing Sheet

(56) References Cited

U.S. PATENT DOCUMENTS

2006/0262139 A1 11/2006 Rahn
2009/0010383 A1* 1/2009 Fuhrmann ............ A61B 6/4441
378/21

FOREIGN PATENT DOCUMENTS

| DE | 102004010205 B3 | 10/2005 |
| DE | 102005022538 A1 | 11/2006 |
| EP | 2149982 A1 | 2/2010 |

* cited by examiner

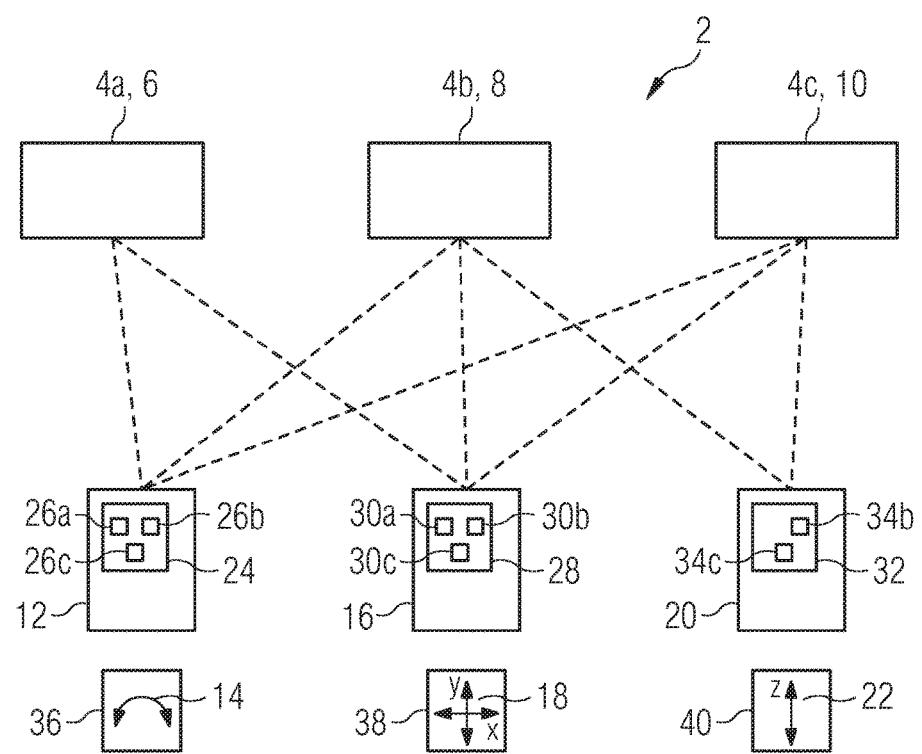

MEDICAL SYSTEM

BACKGROUND OF THE INVENTION

Field of the Invention

The invention relates to a medical system. Such medical systems comprise imaging devices such as x-ray devices or fluoroscopic devices and are used in medical diagnostics. They comprise a plurality of movable elements, for example an x-ray tube, a patient table or else compression elements.

The functionality of medical systems and of the devices integrated in the latter is continuously increasing. This results in their controllers also having to provide more and more functions with respect to the movability of the movable elements as well. Accordingly, the control elements for controlling, in particular, the movements of the movable elements are also becoming more and more numerous and complex. For operators of such medical systems, such as doctors and medical personnel, this offers the chance to perform diagnostics which are more and more individual and adapted to the patient. However, there is also a large risk of losing the overview in such a complex environment. The multiplicity of different devices and movable elements which determine the surroundings of the clinical personnel require simple operation to a particular extent. The desire for simplification and a reduction in the size of the existing control elements, on the one hand, therefore opposes the clear demand for enabling a multiplicity of complex operating functions.

The multiplicity of individual control elements therefore results in the operator losing valuable time again and again in the search for the correct control element. In addition, it is not only the multiplicity of control elements which is a problem, but also the fact that these control elements each have their own, sometimes very different method of operation.

In order to take account of these aspects, an attempt was previously made to reduce the space used by the existing control elements by keeping them as small as possible. An attempt was also made to integrate as many functions as possible into control elements by virtue of them having a plurality of operating levels, for example. However, even with such an approach, a user can spend time looking for the correct functionality on a control element.

BRIEF SUMMARY OF THE INVENTION

Therefore, the object of the present invention is to specify a medical system which is used to avoid the above-mentioned disadvantages and is simplified with respect to its operability.

According to the invention, this object is achieved by means of a medical system having a plurality of movable elements, a first control element for controlling a first type of movement and at least one further control element for controlling a further type of movement. The first control element is assigned to a first number of movable elements for controlling the first type of movement and the further control elements are assigned to a further number of movable elements for controlling the further type of movement. The medical system also comprises at least one input unit which can be assigned to the control elements and has at least two selection elements for selecting the movable element to be controlled.

Such an arrangement of the individual control elements according to the type of movement makes it possible to control the individual movable elements in a uniform and intuitively operable manner.

A control element is therefore used to control a defined type of movement. In this case, a type of movement should be understood as meaning a uniform movement or movement in the same direction. Rotational or tilting movements or planar movements, for example, come into consideration as types of movement. In this case, however, it is also possible to make a finer subdivision into planar movements inside different planes. Such a subdivision can be made in such a manner that, for example, movements inside a plane belong to one type of movement, while movements in a further plane belong to a further type of movement. A type of movement should therefore be respectively understood as meaning a group of movements forming a logical unit in the respective application.

A control element which is used to control a particular type of movement is then assigned to all movable elements which are movable with respect to this type of movement and must be controlled. This means that all movable elements assigned to a particular control element can fundamentally be controlled with respect to this type of movement using said control element. In order to then actually control the movable element in this type of movement using the control element provided for this purpose, the corresponding movable element is selected by the operator for the respective application using the input unit assigned to this control element and the relevant selection element. This means that all movable elements which are assigned the control element can be controlled using the relevant control element. An individual, case-related selection is then made using the input unit and the selection element.

An input unit may also be assigned to a plurality of control elements, for example, with the result that a movable element is selected in different cases with only one input unit using the selection elements.

In one preferred embodiment of the medical system, an input unit is respectively permanently assigned to each control element. This therefore means that each control element has an input unit with corresponding selection elements.

Control is therefore carried out intuitively by virtue of the fact that, in the case of a desired type of movement, the control element provided for this purpose is operated by the operator and the movable element to be controlled is selected using the selection element.

In a basic setting of the medical system, a preselection of one or more movable elements, for example the most frequently used movable elements, can already be preset.

The configuration of the medical system according to the invention therefore means that a plurality of movable elements can be operated with respect to a particular type of movement using only a single control element. The number of operating elements is therefore reduced in comparison with conventional operation during which a separate control element is provided for each movable element.

Despite a multifunctionality of the individual control elements, the complexity of the control element is not increased since only identical movements are combined.

The control of the individual movable elements and therefore of the entire medical system is simplified since there is a clear uniform scheme according to which each individual control element functions.

On account of the uniformity, the operating concept has a high recognition value, thus encouraging intuitive operation.

In addition, it is possible to subsequently add functions in a very simple manner. For example, the range of movement of movable elements can be expanded by then assigning control elements of further types of movement to them. Additional movable elements can likewise be integrated in an existing medical system without the need for further control elements. The already existing control elements are then assigned to these additional movable elements. On account of the multifunctionality of the individual control elements, it is also possible to save a large amount of space, which generally enables a more compact form of the operating components.

In a compact embodiment of the invention, both the control elements and the input unit having selection elements are integrated in a unit having a touchscreen. The individual control elements are then stipulated areas on the touchscreen, with the result that a movement of the movable elements can be controlled by touching said areas. The input unit can also be defined by an area of the touchscreen. For example, the movable elements can be displayed in a thumbnail on the touchscreen and can form this input unit. The respective thumbnail of the movable element illustrated on the touchscreen then constitutes a selection element. Alternatively, however, separate selection elements on the front or rear side of the unit are also possible.

The movable element is preferably those elements of imaging devices such as an x-ray tube or detector, a diaphragm, a camera for real-time recordings or a compression element or a patient table.

A joystick as a control element enables a simple type of control. For example, these joysticks are uniformly configured for all types of movement. However, in order to clearly indicate the individual types of movement, the control elements may have different shapes.

In order to furthermore simplify and also accelerate operation, the selection elements can be used to simultaneously select a plurality of movable elements. This enables a synchronous and simultaneous movement of the plurality of movable elements. Particular parallel movements can even be carried out by the operator using one hand.

For example, a longitudinal movement of a table and of an emitter can take place at the same time. Many further combinations of parallel movements can be carried out. Ideally, it is even possible to carry out individual parallel movements which were not possible at all in current operating concepts. Therefore, mental and motor requirements imposed on the operators are reduced.

If a selection element for the same movable element to be controlled is placed at the same location on the different control elements, the recognition value is increased and yet more intuitive operation is therefore possible.

In order to further assist the operating personnel, a display element which reproduces the associated type of movement is preferably arranged on the control elements. Said display element is therefore used to graphically display the rotational or planar movement, for example.

In addition, in another preferred configuration of the invention, the movable element selected using a selection element can be visualized on the display element. The operator therefore receives feedback relating to which movable element he has selected. Furthermore, the therefore receives an indication of how he can move the specific movable element using the control element.

In order to further simplify the operation, the control element and/or the display element can be adapted to different perspectives of an operator. As a result of such a configuration of the display element, the latter is not statically connected to the control element, but rather can be adapted to different perspectives of an operator, that is to say his viewing directions with respect to the movable element. This means that the display is not static, but rather variable, for example rotatable. The display element then forms, together with the control element to be explained, a closed unit which can be dynamically adapted, however, to the respective situation. The advantages of the display element, on which moving images, arrows or real-time animations can be displayed, are therefore combined with the advantages of a control element which provides the operator with haptic feedback.

The user is therefore presented with a display which is matched to his actual perspective and therefore viewing direction with respect to the movable element to be controlled. Adapting the display element with respect to the user's perspective is so helpful because the operator rarely thinks in technical terms, for example x direction or y direction. Rather, the operator thinks of directions which can be described or perceived as right, left, forward and back from his current perspective.

The above-described properties, features and advantages of this invention and the manner in which they are achieved become clearer and more distinctly comprehensible in connection with the following description of the exemplary embodiments which are explained in more detail in connection with the drawings.

BRIEF DESCRIPTION OF THE SEVERAL VIEWS OF THE DRAWING

For a further description of the invention, reference is made to the exemplary embodiments in the drawings. The single FIGURE shows a basic schematic diagram of:
a medical system according to the invention.

DESCRIPTION OF THE INVENTION

The FIGURE shows a medical system 2 having a plurality of, in this case three, movable elements 4a, 4b, 4c. The movable element 4a is an x-ray tube 6, the movable element 4b is a compression element 8 and the movable element 4c is a patient table 10.

The medical system 2 also comprises a first control element 12 in the form of a joystick which is used to control a first type of movement 14. The first control element 12 is assigned to a first number of movable elements 4a, 4b, 4c for controlling the first type of movement 14. In this case, the first number is therefore three. However, this could be any desired number, depending on the application. The first type of movement 14 is rotational movements in this case. The assignment of the first control element to the movable elements 4a, 4b, 4c is illustrated using the dashed lines. The first control element 12 can therefore be used to control rotational movements in different directions of all movable elements 4a, 4b, 4c, that is to say of the x-ray tube 6, the compression element 8 and the patient table 10, by means of appropriate operation.

The medical system 2 also comprises a further control element 16 in the form of a joystick for controlling a further type of movement 18, in this case planar movements along an x axis and a y axis of the medical system 2. In this exemplary embodiment, the further control element is also assigned to all movable elements 4a, 4b, 4c. The further control element 16 can therefore be used to control planar movements in different directions of all movable elements 4a, 4b, 4c, that is to say of the x-ray tube 6, the compression element 8 and the patient table 10, by means of appropriate operation.

The medical system also has a further control element 20 in the form of a joystick which is used to control a further type of movement 22 which, in this case, allows movements along a z axis of the medical system 2. The further control element 20 is assigned only to the movable elements 4b and 4c since only said elements are movable in such a type of movement 22.

The first control element 12 is permanently assigned an input unit 24 having, in this case, three selection elements 26a, 26b and 26c for selecting the movable element 4a, 4b, 4c to be controlled. The selection element 26a can be used to select the movable element 4a, the selection element 26b can be used to select the movable element 4b and the selection element 26c can be used to select the movable element 4c. The further control element 16 is likewise permanently assigned an input unit 28 having selection elements 30a, 30b and 30c which are likewise used to select the movable elements 4a, 4b, 4c to be controlled. Furthermore, the further control element 20 is also permanently assigned an input unit 32 having selection elements 34b, 34c. In this case, the selection elements 34b and 34c are used to select the movable elements 4b, 4c to be controlled.

In this case, the number of selection elements 26a, 26b, 26c, 30a, 30b, 30c is restricted to three since this is the maximum number before operability becomes too complex for the operator. The selection elements 26a, 26b, 26c, 30a, 30b, 30c, 34b, 34c are actuated, for example, using the index/middle and ring fingers of the operator. The selection elements 26a, 26b, 26c, 30a, 30b, 30c, 34b, 34c may be situated on the rear side or top side of the control element 12, 16, 20.

In order to further simplify operation, the selection elements 26a, 30a or 26b, 34b and 26c, 30c, 34c are each placed at the same location. A recognition effect is therefore increased.

If an operator would now like to carry out a rotational movement of the movable element 4a, he selects the movable element 4a using the selection element 26a of the input unit 24 of the first control element 12. The desired rotational movement of the movable element 4a is now controlled by accordingly moving the control element 12. If the operator would like to carry out a simultaneous rotational movement of the movable elements 4a, 4b, for example, he selects these movable elements 4a, 4b using the selection elements 26a, 26b and can then control a simultaneous movement of the two selected elements by moving the control element 12. As a result of such a configuration of the control of the medical system 2, the operator can save time since operation can be carried out intuitively.

In order to further assist the operator, a display element 36, 38, 40 is respectively arranged on the control elements 12, 16, 20 and reproduces the associated type of movement 14, 18, 22.

The movable element 4a, 4b, 4c selected using the selection element 26a, 26b, 26c, 30a, 30b, 30c, 34b, 34c can also be respectively visualized on this display element. This means that the movable element 4a or the x-ray tube is displayed on the display element 14, for example, if it has been selected for control using the selection element 26a.

The display element 36, 38, 40 or the control element 12, 16, 20 can also be adaptable to different perspectives of an operator.

Although the invention has been specifically illustrated and described in detail by the preferred exemplary embodiment, the invention is not restricted by the disclosed examples and other variations can be derived therefrom by a person skilled in the art without departing from the scope of protection of the invention.

LIST OF REFERENCE SYMBOLS

| | |
|---|---|
| 2 | Medical system |
| 4a, 4b, 4c | Movable element |
| 6 | X-ray tube |
| 8 | Compression element |
| 10 | Patient table |
| 12 | First control element |
| 14 | First type of movement |
| 16 | Further control element |
| 18 | Further type of movement |
| 20 | Further control element |
| 22 | Further type of movement |
| 24 | Input unit |
| 26a, 26b, 26c | Selection element |
| 28 | Input unit |
| 30a, 30b, 30c | Selection element |
| 32 | Input unit |
| 34b, 34c | Selection element |
| 36, 38, 40 | Display element |

The invention claimed is:

1. A medical system, comprising:
    a plurality of movable elements;
    a first control element for controlling a first type of movement of said plurality of movable elements, said first control element being a joystick;
    at least one further control element for controlling a second type of movement of said plurality of movable elements, the first and the second type of movement being mutually different such that a movement of one of said plurality of movable elements controlled by said first control element cannot be controlled by said second control element;
    a first number of said movable elements being configured to be controlled by said first control element according to said first type of movement;
    a further number of said movable elements being configured to be controlled by said at least one further control element according to said further type of movement; and
    at least two input units each having at least two selection elements for selecting said movable elements to be controlled, said input units each being permanently associated with a respective one of said control elements.

2. The medical system according to claim 1, wherein each respective one of said movable elements is an x-ray tube, a compression element or a patient table.

3. The medical system according to claim 1, wherein said at least one further control element is a joystick.

4. The medical system according to claim 1, wherein said first type of movement is a rotational movement and said further type of movement is a planar movement.

5. The medical system according to claim 1, wherein said at least two selection elements are usable simultaneously to select a plurality of said movable elements.

6. The medical system according to claim 1, wherein said at least two selection elements associated with the same movable element to be controlled are placed at the same location on different control elements.

7. The medical system according to claim 1, which further comprises display elements each being disposed on a respective one of said control elements for reproducing an associated type of movement.

8. The medical system according to claim 7, wherein said display elements are each configured to visualize a respective one of said movable elements selected by one of said at least two selection elements.

9. The medical system according to claim 7, wherein at least one of said control elements or said display elements can be adapted to different perspectives of an operator.

* * * * *